United States Patent [19]
Rudd et al.

[11] Patent Number: 5,250,431
[45] Date of Patent: Oct. 5, 1993

[54] ALTERATION OF THE INTERACTION OF A T-CELL RECEPTOR WITH A PROTEINTYROSINE KINASE

[75] Inventors: Christopher Rudd, Somerville; Stuart Schlossman, Newton Center, both of Mass.

[73] Assignee: Dana-Farber Cancer Institute, Inc., Boston, Mass.

[21] Appl. No.: 759,639

[22] Filed: Sep. 12, 1991

Related U.S. Application Data

[63] Continuation of Ser. No. 206,003, Jun. 13, 1988, abandoned.

[51] Int. Cl.$^5$ .............. C12N 5/00; C12N 15/00; C07K 13/00
[52] U.S. Cl. ............... 435/240.2; 435/69.1; 435/172.3; 530/350; 935/70; 935/71; 935/10
[58] Field of Search .......... 530/350, 351, 387; 435/69.1, 172.3, 240.2, 317.1; 935/70, 71, 11, 111, 10

[56] References Cited

PUBLICATIONS

Rudd et al., Cellular Basis of Immune Modulation 9: 79–91 (1988).
Smith et al., Science 238: 1704–1707 (1987).
European Search Report EP 89305907, dated May 15, 1991.
Sleckman et al. (a), Nature 328: 351–353 (1987).
Sleckman et al. (b), J. Immunology, 141: 49–54 (1988).
Maddon et al., Cell 42: 93–104 (1988).
Trevillyan et al., Bioch. Biophy. Acta 888: 286–295 (1986).
Kunkel, Proc. Natl. Acad. Sci. 82: 488–492 (1985).
Hatakeyama et al., Nature 318: 467–470 (1985).
Beiger et al., Proc. Natl. Acad. Sci. 85: 2357–2361 (1988).
Traunecker et al., Nature 331, 84–86 (1988).
Bedinger et al., Nature 334: 162–165 (1988).
Clayton et al., Nature 335: 363–366 (1988).
Davis, Ciba Found. Symp. 130: 34–51 (1987).
Kondo et al., Nature 327: 64–67 (1987).
"Oncogenes and Growth Control", ed. Kohn & Graf, Springer-Verlag, Heidelberg (1986), pp. 108, 135–139.
Veillette et al., Eur. J. Immunol. 20: 1397–1400 (1990).
Barber et al., Proc. Natl. Acad. Sci. 86: 3277–3281 (1989).
Shaw et al., Mol. Cell. Biol. 10(5): 1853–1862 (1990).
Turner et al., Cell 60: 755–765 (1990).
Glaichenhaus et al., Cell 64: 511–520 (1991).
Marth, et al., Cell, vol. 43, 393 (1985).
Koga, et al. Eur. U. Immunol. vol. 16, 1643 (1986).
Maddon et al., 47 Cell 333, (1986).
Sleckman et al., 328 Nature 351 (1987).
Madden et al. 42 Cell 93 (1985).
Fisher et al., "HIV Infection is Blocked in Vitro by Recombinant Soluble CD4", Nature vol. 331, pp. 76–78 (Jan. 7, 1988).

*Primary Examiner*—Jasemine C. Chambers
*Attorney, Agent, or Firm*—Fish & Richardson

[57] ABSTRACT

This invention concerns alteration of the interaction of PTKs and T-cell receptors. We have found that PTKs and T-cell receptors are complexed within the T-cell and the formation of this complex dictates the susceptibility of the T-cell to activation and to infection by viruses such as HIV. The nature of the interaction between the kinase and the T-cell receptor in a human is also related to the potential for cancer cell formation in that human, and to susceptibility to an autoimmune disease. Modified CD4 and CD8 T cell receptors and transfected mammalian cells expressing the same are disclosed.

18 Claims, No Drawings

ALTERATION OF THE INTERACTION OF A T-CELL RECEPTOR WITH A PROTEINTYROSINE KINASE

This invention was made with support from the National Institute of Health, grant numbers AI 12069 and R23 AI 23992. The U.S. Government has rights in the invention.

This application is a continuation of application Ser. No. 07/206,003, filed Jun. 13, 1988, now abandoned.

BACKGROUND OF THE INVENTION

This invention concerns alteration of the interaction of a T-cell receptor and a protein-tyrosine kinase.

T-cells express cell surface antigens, e.g., CD4, and CD8 which are implicated in regulation of T-cell activation and in the association and recognition of specific antigens. CD4, which is a polypeptide antigen of 55 kDa, appears to serve as a receptor for the human immunodeficiency virus (HIV). Maddon et al., 47 Cell 333, 1988, Sleckman et al., 328 Nature 351, 1987. Structurally, the CD4 antigen is a member of an immunoglobulin superfamily (Maddon et al,, 42 Cell 93, 1985) and appears capable of regulating the proliferation of the CD4 subset of T-cells. CD8 has a molecular weight of 32 kDa and is also a member of the immunoglobulin superfamily. It appears to be involved in the recognition of major histocompatibility complex (MHC) class I antigens. It defines a separate population of T-cells distinct from the CD4 subset. The CD4 and CD8 antigens may also regulate the activation of T-cells, either individually, or in conjunction with the antigen CD3-Ti present on the surface of T-cells.

Protein-tyrosine kinases (PTKs) play a role in activation and transformation of mammalian cells. For example, oncogenic transformation by Rous sarcoma virus is mediated by the PTK, pp $60^{src}$. Several retroviral ongogenes are homologous to pp $60^{src}$ and together form a family of src-like PTKs. These include v-abl, v-erb, v-fes/fps, V-fgr, v-src and v-yes. Also within this family are the receptors for epidermal growth factor, platelet-derived growth factor, and insulin. Another homologous protein kinase, termed pp $56^{lck}$, (or p$56^{Lstra}$, p$58^{lck}$) has been identified in murine T-cells (Marth et al., 43 Cell 393, 1985), as has its homolog in human T lymphocytes (Trevillyan et al., 888 Bioc. Biop. Acta. 286, 1986, and Koga et al., 16 Eur. J. Immumol. 1643, 1986). PP $56^{lck}$ may decrease in amount in T-cells after their activation, however its role in the process is unknown.

SUMMARY OF THE INVENTION

This invention concerns alteration of the interaction of PTKs and T-cell receptors. We have found that PTKs and T-cell receptors are complexed within a T-cell and that the formation of this complex dictates the susceptibility of the T-cell to activation, and to infection by viruses such as HIV. The amount of this complex in a human is also related to the potential for cancer cell formation in that human, and to the potential to succumb to an autoimmune disease, or an autoimmunodeficiency disorder including disorders which involve interaction with virus (e.g., HIVI) or an MHC class II antigen (e.g, diabetes).

In a first aspect, the invention features a modified T-cell receptor, (e.g., CD4, or CD8) or a protein tyrosine kinase (PTK) having an altered binding capability, compared to the corresponding naturally occurring T-cell receptor or PTK, for a PTK or T-cell receptor naturally associated with the naturally occurring T-cell receptor or PTK. That is, the level of binding may decrease, increase or be the same. In the latter case, the activity of the kinase is decreased, or its level of interaction with other intracellular molecules is reduced.

In related aspects, the invention features a cell (e.g., a T-cell) or a transgenic animal (e.g., a mouse) having the above-described modified T-cell receptor or PTK.

In one preferred embodiment, the modified T-cell receptor is a modified CD4, or CD8 having an altered cytoplasmic tail; the modified CD4, or CD8 is unable to bind to a PTK. In another preferred embodiment, the modified PTK is unable to bind to CD4 or CD8. In each case, the T-cell is resistant to HIV infection, binding or replication.

In another aspect, the invention features a modified kinase, the kinase affecting binding of a PTK with a T-cell receptor, such as CD4 or CD8, wherein the modified kinase is reduced in its ability, compared to naturally occurring kinase, to affect such binding.

In preferred embodiments, the PTK is a substrate for the kinase, and phosphorylation by the kinase affects the binding of the PTK to the T-cell receptor. For example, the modified kinase is protein kinase C.

In another aspect, the invention features antisense mRNA having homology to mRNA transcribed from DNA encoding a T-cell receptor or a PTK.

In another aspect, the invention features a transgenic animal, wherein the naturally occuring animal is resistant to infection with HIV, and wherein the transgenic animal is sensitive to infection.

In preferred embodiments, the transgenic animal is a mouse; the transgenic animal includes a T-cell receptor, (e.g., CD4 or CD8) and a PTK naturally associated with the T-cell receptor in a T-cell of a human.

In another aspect, the invention features a method for treatment of a patient having an autoimmune disorder or a cancer, including the step of altering the normal level of interaction of a PTK with a T-cell receptor in a T-cell of the patient.

In preferred embodiments, the disorder is infection with HIV, Systemic Lupus, Erythmatosis, Multiple Sclerosis, Juvenile Diabetes Mellitus or rheumatoid arthritis; the reducing step includes providing a T-cell having an altered T-cell receptor, with a reduced ability to bind to a naturally occurring PTK; or providing a T-cell having an altered PTK, with a reduced ability to bind to a naturally occurring T-cell receptor; or replacing or supplementing the T-cells of the patient with a T-cell having an altered T-cell receptor or PTK as described above; or providing an altered T-cell receptor having an enhanced ability to bind a PTK; or replacing or supplementing the T-cells of the patient with a T-cell resistant to infection by HIV; or providing antisense mRNA able to bind to mRNA encoding a T-cell receptor or a PTK; or providing an inhibitor of a PTK, most preferably the inhibitor is chosen from p-fluorosulfonyl-benzoyl-denosine (FSBA), or another ATP analog, a halomethylketone, amiloride, a mitogen, the dipeptide tyr.arg, or a peptide which competes for phosphorylation of a substrate; or changing the level of phosphorylation of the PTK in vivo.

In another aspect, the invention features a method for screening a human for susceptibility to a cancer, including determining the level of a PTK in the patient. A level or activity of a PTK higher than the average level in a population of humans is indicative of susceptibility to cancer.

In yet another aspect, the invention features a method for treatment of a patient with a cancer, including providing the patient with a reagent able to block interaction of a PTK and a T-cell receptor.

Other features and advantages of the invention will be apparent from the following description of the preferred embodiments thereof, and from the claims.

DESCRIPTION OF THE PREFERRED EMBODIMENTS

T-cell receptors

T-cell receptors are well-known to those in the art. For example, CD4 is a T-cell receptor, and is described above. Another receptor useful in this invention is CD8 (Littman et al., 40 Cell 237, 1985; Suhkative et al., 40 Cell 591, 1985). Those other receptors useful in this invention can be identified by standard procedure, an example of which is presented below. Generally, any T-cell receptor which is associated in vivo with a PTK is useful in this invention.

Protein-tyrosine kinases (PTKs)

PTKs are involved in phosphorylation of tyrosine residues in proteins. Generally, adenosine triphosphate (ATP) is used in this process. They also possess the property of autophosphorylation.

A human cDNA clone encoding a PTK is described by Koga et al., 16 Eur. J. Immunology 1643, 1986, hereby incorporated by reference herein. This PTK appears to be the human homolog of a murine PTK (Marth et al. 43 Cell 393, 1985, and Koronova et al., 319 Nature 682, 1986; both hereby incorporated by reference herein).

Generally, any PTK which is associated specifically in vivo with a T-cell receptor is useful in this invention. An example of identification of such PTKs is given below. This example is not limiting to the present invention.

EXAMPLE

Interaction of CD4 and PTKs

CD4 is complexed in detergent lysates from T-lymphocytes with at least one PTK of 55-60 kDa having homology to c-src and c-yes. The PTK can be identified by use of antiserum against a synthetic peptide deduced from the DNA sequence of the PTK, as follows.

A monoclonal antibody against the CD4 antigen 19 thy 5D7 (IgG2) was raised as described by Reinherz et al., 74 Immunol. Rev. 83, 1983, hereby incorporated by reference herein. This antibody was used to precipitate CD4 antigen from unlabelled peripheral blood lymphocytes. The blood lymphocytes were isolated by Iso-Hypaque centrifugation and used either as resting cells or stimulated with Con A (5 µg/ml, Sigma) for 24-36 h. The CD4 antigen was also precipitated from the generally available transformed cell lines HPB-MLT, REX, the B-lymphobastoid cell line Raji, and the myeloid cell line U937. All cell lines were cultured in RPMI 1640 medium with 10% (vol/vol) fetal calf serum and 1% (wt/vol) penicillin/streptomycin at 37° C. in 5% $CO_2$/95% air. The immunoprecipitations were performed by solubilizing cells at $25\times10^6$ cells/and in Nonidet NP-40 lysis buffer (1% (vol/vol) in 3% (vol/vol), Nonidet P-40 in 20 mM tris. HCl buffer, pH 8.0/150 mM NaCl, 1 mM phenylmethylsulfonyl fluoride) for 30 min at 4° C., as described by Rudd et al., 260 J. Biol. Chem. 1927, 1985. The lysate was centrifuged at $12,000\times g$ and precleared for 30 min. with 50 µl of 10% (wt/vol) Staphylococcus Cowan strain 1. The lysate was then incubated for 1-2 hr. at 4° C. with either 5 µl of ascites fluid and 50 µl of 10% (wt/vol) protein A-Sepharose or 50 µl of 10% (wt/vol) protein A-Sepharose (cross-linked to antibody by the method of Schneider et al., 275 J. Biol, Chem. 10,766, 1982).

The immunoprecipitates were washed three times with Nonidet P-40 lysis buffer prior to incubation with 30 µl of 25 mM Hepes containing 0.1% (vol/vol) Nonidet P-40, 10 µM ATP, and 1-10 µCi of [$\gamma$-$^{32}$P]ATP (1 Ci=37 GBq; ICN Chemicals). After an incubation of 15-30 min. at 25° C., the reaction mixture was subjected to $NaDodSo_4$/PAGE and autoradiography. For the analysis of reprecipitated antigen, the reaction mixture was supplemented to 1.0 or 2.0% (wt/vol) $NaDodSO_4$ boiled and diluted with a 1:10 or 1:20 dilution of lysis buffer to a final concentration of 0.1% $NaDodSO_4$ before re-precipitation. Two-dimensional nonequilibrium pH gradient gel electrophoresis (NEPHGE) $NaDodSO_4$/PAGE was conducted with ampholines of a pH range between 2 and 11 as described by Rudd et al., 260 J. Biol. Chem. 1927, 1985.

The immunoprecipitates were then assessed for their ability to phosphorylate polypeptides (i.e., for kinase activity) during an incubation with [$\gamma$-$^{32}$P]ATP. The anti-CD4 antibody precipitated several polypeptides at 38 and 55-60 kDa from both resting and Con A-activated cells, which were phosphorylated in the presence of [$\gamma$-$^{32}$P]ATP. The bands at 55/60 kDa were found to be more intense on a per cell basis from Con A-activated cells than from resting lymphocytes. The anti-CD4 antibody was also found to precipitate a similar pattern of bands within the 55- to 60-kDa range from the human T-lymphoblastoid cells lines Rex and HPB-MLT. However, in this case, the presence of the polypeptide at 38 kDa was somewhat variable. In addition, an extra band at $\approx 80$ kDa was often observed. Neither the myeloid cell U937 nor the B-lymphoblastoid cell Raji, which have been reported to express the CD4 antigen, was found to precipitate significant amounts of material labeled by [$\gamma$-$^{32}$P]ATP. A faint amount of material at 50 kDa was occasionally observed from Raji cells; however, the position of this polypeptide was different from that observed from the T lymphocytes. As a negative control, the monoclonal antibody W6/32, which reacts with class I antigens of the major histocompatibility complex at 45 and 12 kDa, was unable to precipitate material capable of being labeled from the various cells. Other monoclonal antibodies against antigens on T cells such as the T3 (CD4) complex, the T11 (CD2) antigen, HLA-D region antigens, and fibronectin receptor/VLA antigens (4B4) also failed to precipitate material capable of being labeled under this regime. Thus, kinase activity associated with CD4 appears to be T-cell specific.

Analysis of phosphorylated amino acids was then carried out to investigate the nature of amino acid residues that were phosphorylated with [$\gamma$-$^{32}$P]ATP. Proteins were eluted from fixed polyacrylamide gels and precipitated with trichloracetic acid as described by Swarup et al., 258 J. Biol. Chem. 1034, 1983. The precipitate was washed in acetone and hydrolyzed in 6M HCl at 100° C. for 2 hr. The individual phosphorylated amino acids were separated by electrophoresis (2500 V, 30 min.) at pH 3.5 in pyridine/acetic acid/water (1:10:189; vol/vol). Nonradioactive standards were detected with ninhydrin, while radiolabeled phosphorylated amino acids were observed by autoradiography. Bands at 55/60 kDa, which were precipitated by the anti-CD4 antibody, were heavily phosphorylated at one or more tyrosine residues and to a much lesser extent at one or more serine residues. The presence of a phosphoserine residue on the CD4 antigen has been detected by in vivo labeling techniques and is consistent with the presence of a serine in the cytoplasmic tail of the antigen. However, based on its DNA sequence, the cytoplasmic tail of CD4 lacks a site for tyrosine phosphorylation, as well as a tyrosine kinase domain. These data argue that the 55- to 60-kDa band is unlikely to correspond to the CD4 receptor, and, instead, suggest that the 55- to 60-kDa band is a PTK and/or a substrate for the protein kinase that coprecipitates with the CD4 antigen.

To establish which PTK was associated with the CD4 antigen, an antiserum that had been raised in rabbits against a synthetic peptide (Cys-Lys-Glu-Arg-Pro-Glu-Asp-Arg -Pro-Thr-Phe-Asp-Tyr-Leu-Arg-Ser-Val-Leu-Glu-Asp-Phe-Phe-Thr-Ala-Glu -Gly-Gln-Tyr-Gln-Pro-Gln-Pro), corresponding to the C-terminus of the human tyrosine kinase corresponding to pp 56$^{lck}$, was used in immunoprecipitation analysis and compared with precipitates formed by a monoclonal antibody against the CD4 antigen. The generation of antiserum is generally described by Trevillyan et al., 140 Bioc. Biop. Res. Comm. 392, 1986. The immunoprecipitates produced a spectrum of phosphorylated bands with molecular sizes of about 40, 55, and 60 kDa. However, differences were noted in the relative intensities of the bands in the pattern, dependent upon the antibody used. Anti-CD4 immunoprecipitates showed greater amounts of phosphorylation of 55- and 60-kDa bands relative to the 40-kDa band, while anti-PTK immunoprecipitates showed greater amounts of phosphorylation of the 40-kDa than the 55- and 60-kDa bands. The anti-PTK antibody was unable to precipitate material from B cells. As an internal control for tyrosine phosphorylation, each of the immunoprecipitates was found to label enolase, which was added as substrate during the labeling procedure. Thus, the similarity of patterns suggests that a common spectrum of polypeptides is associated with the anti-CD4 and the PTK immunoprecipitates.

A direct demonstration of the association was shown by denaturing the phosphorylated immunoprecipitates in the presence of NaDodSO$_4$ and then attempting to reprecipitate with the reciprocal antibody (i.e., anti-CD4 followed by anti-PTK, or vice versa) as follows. Immunoprecipitates derived from peripheral blood lymphocytes that had been stimulated with Con A for 12 hr were used in a kinase assay. Enolase (1–2 μg; Sigma) was added as substrate before addition of the reaction mixture. An immunoprecipitate was formed by an anti-CD4 antibody and subjected to in vitro phosphorylation with [$^{32}$P]ATP. The anti-CD4 immunoprecipitation was then denatured in either 1% (wt/vol) or 2% (wt/vol) NaDodSo$_4$ and reprecipitated with the anti-PTK antibody. Conversely, a cocktail of anti-CD4 antibodies (12T4D11, 18T3A9, 19thy5D7) was found to reprecipitate a very faint band from the phosphorylated precipitates formed by the anti-PTK antiserum. In neither case was the control antibody, 1F7, found to reprecipitate antigen. The specificity in the recognition by the antibody of the polypeptides was shown by the ability of the above synthetic peptide to block the precipitation by anti-PTK antiserum, but not by the anti-CD4 antibody. Subsequent phosphorylated amino acid analysis of the reprecipitated PTK antigen by the anti-PTK antiserum detected radiolabel at a tyrosine residue. These data demonstrate that the 55- to 60-kDa bands corresponds primarily to the autophosphorylation of the T-cell-specific PTK, which coprecipitated with the CD4 receptor.

Two-dimensional non-equilibrium pH gradient gel electrophoresis (NEPHGE/NaDodSo$_4$/PAGE) was conducted to compare the identity and structure of the PTK associated with the CD4 antigen with that recognized directly by the anti-PTK antiserum in cells. The anti-PTK antiserum and the anti-CD4 antibody were used to precipitate antigen from from Con A-stimulated peripheral blood lymphocytes. Immunoprecipitates were then subjected to labeling with [$^{32}$P]ATP. The labeled polypeptides were eluted from protein A-Sepharose beads by boiling in the presence of 1% (wt/vol) NaDodSO$_4$ for 5 min. and diluted 1:10 in Nonidet P-40 lysis buffer. The anti-PTK antiserum was then used to precipitate antigen from these preparations followed by three washes in lysis buffer and two-dimensional NEPHGE/NaDodSO$_4$/PAGE. The polypeptide reprecipitated by the anti-PTK antiserum from a denatured anti-CD4 immunoprecipitate focused as two separate series of spots of slightly different molecular sizes and isoelectric positions over a pH range of 4.0–5.0. This pattern was similar to that observed when the anti-PTK antiserum was used to reprecipitate PTK from denatured anti-PTK immunoprecipitates. The only detectable difference in the two patterns was that the pattern derived from the anti-CD4 precipitate appeared to extend over a slightly smaller pH range than that recognized by the anti-PTK antiserum. These data confirm that the PTK associated with the CD4 receptor is a member of the series of spots recognized by the anti-PTK antiserum.

The PTK described above belongs to a family of PTKs that generally comprise a portion of the cytoplasmic tail of the epidermal growth factor, insulin, and platelet-derived growth factor receptors. In this case, however, the PTK lacks a recognizable transmembrane domain, and instead, may function by means of an association with the CD4 antigen. The NEPHGE/NaDodSO$_4$-PAGE pattern revealed a heterogeneity of spots, a result consistent with either differences in the degree of phosphorylation of an individual PTK and/or the presence of a family of related PTKs. In either case, this association represents the first case of an association between a receptor on the surface of T-cells and a member of a family of intracellular mediators with an ability to activate and transform cells.

It appears unlikely that the association is an artifact of detergent lysis since immunoprecipitates of numerous other T-cell antigens, including the T3 (CD3) subunits, the T11 (CD2) antigen, the T200/L-C (CD45) antigens, and the fibronectin receptor, failed to produce detectable kinase activity.

Other T-cell receptors and PTKs useful in this invention can be identified and isolated by similar techniques. For example, the antibody used in the example above can be used to identify other PTKs, as long as the amino acid sequence recognized by the antibody is present on the PTK. Similarly, other PTKs can be discovered by looking for those which bind specifically to the cytoplasmic tail of a T-cell receptor, such as CD4. For example, the cytoplasmic region of CD4 can be removed by standard protein techniques, or cloned and expressed by standard techniques in a retroviral vector, and this region used to purify a PTK.

Methods

As described above, applicant has recognized that the interaction of a PTK with a T-cell receptor is important in susceptibility of T-cells to viruses, such as HIV. Further, such interactions are important in susceptibility of animals, such as humans, to development of cancers. That is, a high level of PTKs in a human is indicative of susceptibility of that human to a cancer. Other autoimmune disorders are also related to this interaction, e.g., systemic lupus and rheumatoid arthritis.

In addition the CD3/Ti complex appears to be involved in regulation of the function of T-cells, which appears to involve an interaction with the CD4/CD8 receptors. These receptors may recognize MHC antigens associated with the Ti/CD3 complex. A physical association between CD4/CD8 and the Ti/CD3 complex has never been directly demonstrated, however it has been implied in co-modulation studies (Saizawa et al., 328 Nature 260, 1987). The interaction may therefore occur within the cytoplasm of the cell i.e., between the cytoplasmic tail of CD4/CD8 and that of CD3/Ti via p 58$^{lck}$. Such an interaction may be key to the mechanism by which T-cells are activated and induced to carry out their immune function. Thus a PTK e.g., p58$^{lck}$, associated with a T-cell receptor e.g., CD4/CD8, may form the biochemical linkage (either a physical linkage or a signal-type linkage) between CD4/CD8 and the Ti/CD3 receptor complex. The interaction may regulate the activation or down-regulation of activation of T-cells by foreign antigens. It is this linkage that is disrupted in this invention.

This invention features methods for treating, or diagnosing, the above-mentioned diseases by changing the interaction of a PTK with a T-cell receptor, or reducing the enzymatic activity of the PTK itself. Such methods are generally performed by standard techniques. A few examples are given below; these are not limiting to the invention.

Altered T-cell Receptor or PTK Molecules

The specific T-cell receptor or PTK molecule involved in the interaction and associated with disease susceptibility can be altered by several standard techniques. For example, the protein molecule may be purified away from its natural environment and treated with proteases to remove specific portions. Alternatively, the amino acid sequence of the protein can be determined and synthetic sequences prepared which lack the specific polypeptide sequence involved in the interaction. The DNA sequence of the protein-encoding gene may also be determined and mutations created by in vitro mutagenesis (see e.g., Ellis et al., 45 Cell 721, 1986, Marth et al., 8 Mol. Cell. Biol. 540, 1988, and Ellis et al., 45 Cell 721, 1986), by restriction enzyme digestion, or by creation of a short deletion. One example of a deletion is described in the CD4 molecule by Slechman et al., J. Immunology (July, 1988) where 31 amino acids in the cytoplasmic domain were deleted by treatment of CD4 cDNA with NarI, resection of the protruding end with T4 DNA polymerase, and ligation to a filled in NheI site. Similarly, expression of these genes may be altered by mutating the transcriptional or translational control signals, or other such expression signals, as described by Voronova et al., 319 Nature 692, 1986, and by Marth et al., 332 Nature 171, 1988, and 43 Cell 393, 1985.

Generally, it is desirable to delete the region of amino acids in the protein involved in interaction with the other protein of the T-cell receptor-PTK binding pair. This region of interaction can be identified by standard biochemical techniques. Generally, this region involves the cytoplasmic tail of the T-cell receptor. Further, mutations which affect the in vivo conformation of this region are also useful. Standard procedures are used to identify useful mutations using in vitro or in vivo methodology. For example, a library of clones encoding mutated PTK genes can be transfected into a T-cell having a normal CD4 molecule and a normal PTK molecule. Such cells will generally be sensitive to infection by HIV. Clones which reduce this sensitivity are useful in this invention. Those clones will encode a PTK which affects the binding of HIV to the CD4/PTK complex, for example, by competing with the normal PTK for binding with CD4, and the complex so formed not being recognized by HIV as an appropriate target molecule.

In another example, a series of mutated genes can be placed into a retroviral expression vector, such as SV40 (Okayama et al., 3 Mol. Cell. Biol. 280, 1983; and Sleckman et al., 328 Nature 351, 1987) and T-cells, which may or may not contain CD4 and/or a PTK, and B-cells (lacking PTK) transfected. Those cells will then be screened to discover whether they are resistant to infection by HIV, binding with HIV, or replication of HIV using standard techniques.

In a more specific example, a site in the T-cell receptor, CD4 and CD8, has an 13 amino acid region involved in binding with a PTK. The site involves the amino acid sequence of CD4: KKTCQCPHRFQKT (using the standard code for amino acids), and of CD8:RRVCKCPRPVVKS. In p58$^{lck}$ the N-terminal region is involved in interaction with CD4 or CD8. These regions are preferably removed or altered to produce a protein useful in this invention.

In another category of potentially useful altered molecules, those involved in processing the T-cell receptor or PTK can also be used in this invention. For example, protein kinase C phosphorylates proteins, such as the human PTK described above. Thus, alteration of the activity of protein kinase C by mutation, or otherwise, to prevent phosphorylation of PTK will effectively affect the interaction of PTK with a T-cell receptor. See e.g., Piwnica-Worms et al., 49 Cell 75, 1987, where p60$^{sic}$ is altered. A similar alteration to p58$^{lck}$ may affect binding to CD4 or CD8.

Inhibitors

Inhibitors of the activity of PTKs can be used to reduce the susceptibility of T-cells to viral infection, or to reduce the susceptibility of a human to cancer formation or an autoimmune disease. Such inhibitors may also prevent autophosphorylation of PTKs and thus affect their interaction with a T-cell receptor. Examples of such inhibitors include: the ATP analog FSBA which irreversibly inhibits PTKs by binding at the ATP-binding site (Zoller et al., 256 J. Biol. Chem. 10837, 1981; and Kamps et al., 310 Nature 589, 1984); halomethylketones (Nararro et al., 21 Biochem. 6138, 1982); quercetin (Graziani et al., 135 Eur. J. Biochem. 583, 1983; and Cochet et al., 31 Bioc. Pharma. 1357, 1982); amiloride, an inhibitor of passive Na$^+$ uptake (Davis et al., 260 J.

Biol. Chem. 2543, 1985); Ap4A (Maness et al., 258 J. Biol. Chem. 4055, 1983); dipeptides such as tyr.arg (kyotorphin; Braun et al., 259 J. Biol. Chem. 2051, 1984); and various peptides which compete for phosphorylation of substrates (Wang et al., 78 Proc. Nat. Acad. Sci. USA 7412, 1981).

These inhibitors can be provided as therapeutic agents to inhibit PTK activity or reduce interaction of a PTK and a T-cell receptor using standard therapeutic techniques. For example, FSBA can be provided in a therapeutically acceptable composition at a dose of between 10–1000 μg/Kg body weight of a human and maintained at a therapeutic level by daily doses.

Activators are also useful in this interaction where they so affect the activity of a PTK that interaction with a T-cell receptor is affected.

Suitable inhibitors and activators can be determined by screening for the affect of the inhibitor or activator on PTK activity using standard kinase assays, as described above, and by Swarup et al., 258 J. Biol. Chem. 10,341, 1983.

Another useful inhibitor is antisense mRNA produced by causing transcription of the nonsense strand of DNA encoding a T-cell receptor or PTK. The normal mRNA will bind to this antisense mRNA and translation of the normal mRNA prevented. Any antisense mRNA with sufficient homology to bind the normal mRNA is useful in this invention. Generally, a vector encoding the antisense mRNA is transfected into a T-cell, and expression of the antisense mRNA prevents expression of the T-cell receptor or PTK. In this way, e.g., CD4 or PTK expression in a T-cell is prevented and a T-cell line lacking CD4 and/or PTK produced.

Uses

Any of the above-described methods of altering PTK-T-cell receptor interaction or the individual expression of the PTK or T-cell receptor can be used in therapeutic or diagnostic methods. Similarly, alteration of the interaction of thse molecules with other antigens, e.g., Ti/CD3, is useful in affecting susceptibility of a T-cell to diseases or viral infection. For example, the above-mentioned inhibitors can be used as discussed above. Similarly, the altered T-cell receptor or PTKs can be used therapeutically to reduce, e.g., HIV infectivity. Useful cell lines can also be created. Such cell lines include T-cells lacking, or unable to express, either a T-cell receptor, e.g., CD4, or a PTK. These cells may be used to reconstitute the T-cells of an HIV-infected (or other virally immunosuppressed) patient, or one suffering from a cancer or autoimmune disease. Cell lines having a CD4 molecule with an increased affinity for PTK are also useful since this may provide an altered signal to the T-cell containing it, such that activation of the T-cell is affected.

In one example, precursor T-cells can be created which lack CD4 on their cell surface. These cells are then transfected with an altered gene encoding a CD4 unable to bind a PTK, and the cells treated with interleukin 2. Antisense CD4-encoding DNA is also introduced into these cells so that expression of the normal CD4 molecule in those cells is inhibited. Such cells are HIV resistant, and can be used to replace the immune system of an HIV-infected human.

The above techniques can also be used to form a useful animal-model system for HIV. To date no convenient animal model exists. Mouse cells are naturally resistant to HIV infection, even when provided with CD4 molecules. Mouse cells can be transfected with both a PTK and a CD4 molecule to form an HIV sensitive cell. Using the techniques described by Leder et al. (U.S. Pat. No. 4,736,866, hereby incorporated by reference herein) transgenic mice having CD4 and PTK on their T-cell surfaces can be created. Such mice can be used to study HIV infectivity.

Another use involves diagnosis of persons susceptible to a cancer. Such persons have elevated levels of a PTK in their T-cells. Thus, standard immunoassays can be performed to screen a person for greater than normal PTK levels. Those persons having elevated PTK levels can be treated by agents which block PTK activity or prevent PTK-T-cell receptor interaction, as described above. Similarly, such treatments are useful for patients with autoimmune diseases.

The above therapies can be used in conjunction with transplantation techniques presently being employed. For example, monoclonal antibodies, such as B-1 or T12, are used in bone marrow transplantation programs to purge malignant lymphomas or leukemic cells. The use of agents which affect the association of a PTK, e.g., $58^{lck}$, with a T-cell receptor e.g., CD4/CD8, and its subsequent interaction with another antigen, such as CD3/Ti, may enhance the reconstitution of transplanted normal cells. Alternatively, the combined use of monoclonal antibodies in immunotherapy with reagents which affect the PTK association with a T-cell receptor will form useful immunotherapeutic tools. They are also useful immunosuppressive agents.

Other embodiments are within the following claims.

We claim:

1. A modified CD4 T cell receptor having a reduced binding capability, compared to that of naturally occurring CD4 T cell receptor, for $p56^{lck}$, wherein said modified receptor has an alteration or deletion in the $p56^{lck}$ binding site located on the cytoplasmic tail of said naturally occurring CD4 T cell receptor.

2. A modified CD8 T cell receptor having a reduced binding capability, compared to that of naturally occurring CD8 T cell receptor, for $p56^{lck}$, wherein said modified receptor has an alteration or deletion in the $p56^{lck}$ binding site located on the cytoplasmic tail of said naturally occurring CD8 T cell receptor.

3. The modified receptor of claim 1, wherein said modified receptor lacks said binding site.

4. The modified receptor of claim 2, wherein said modified receptor lacks said binding site.

5. The modified receptor of claim 1, wherein said modified receptor is unable to bind to $p56^{lck}$.

6. The modified receptor of claim 2, wherein said modified receptor is unable to bind to $p56^{lck}$.

7. The modified receptor of claim 1, wherein said modified receptor comprises a transmembrane sequence of CD4.

8. The modified receptor of claim 2, wherein said modified receptor comprises a transmembrane sequence of CD8.

9. The modified receptor of claim 7, wherein said modified receptor lacks said binding site.

10. The modified receptor of claim 8, wherein said modified receptor lacks said binding site.

11. The modified receptor of claim 7, wherein said modified receptor lacks or has an alteration in the amino acid sequence KKTCQCPHRFQKT of naturally occurring CD4 T cell receptor.

12. The modified receptor of claim 8, wherein said modified receptor lacks or has an alteration in the amino acid sequence RRVCKCPRPVVKS of naturally occurring CD8 T cell receptor.

13. A mammalian cell transfected with DNA encoding the modified receptor of claim 1 and expressing on its surface the modified receptor of claim 1.

14. A mammalian cell transfected with DNA encoding the modified receptor of claim 2 and expressing on its surface the modified receptor of claim 2.

15. The cell of claim 13, said cell being a T cell.

16. The cell of claim 14, said cell being a T cell.

17. The cell of claim 13, wherein said modified receptor lacks said binding site.

18. The cell of claim 14, wherein said modified receptor lacks said binding site.

* * * * *

UNITED STATES PATENT AND TRADEMARK OFFICE
CERTIFICATE OF CORRECTION

PATENT NO. : 5,250,431
DATED : October 5, 1993
INVENTOR(S) : Christopher Rudd, et. al.

It is certified that error appears in the above-indentified patent and that said Letters Patent is hereby corrected as shown below:

On the Title page, item [75], inventors: insert--Christopher Rudd, Somerville, Mass.; Stuart Schlossman, Newton Center, Mass.; and Steven Bruakoff, W. Newton, Mass.

Signed and Sealed this

Twentieth Day of September, 1994

Attest:

BRUCE LEHMAN

Attesting Officer          Commissioner of Patents and Trademarks

UNITED STATES PATENT AND TRADEMARK OFFICE
CERTIFICATE OF CORRECTION

PATENT NO. : 5,250,431

DATED : October 5, 1993

INVENTOR(S) : Christopher Rudd et al.

It is certified that error appears in the above-identified patent and that said Letters Patent is hereby corrected as shown below:

On the Title Page, item [75], inventors: insert--Christopher Rudd, Somerville, Mass.; Stuart Schlossman, Newton Center, Mass.; and Steven Burakoff, W. Newton, Mass.

This certificate supersedes certificate of correction issued September 20, 1994.

Signed and Sealed this

Fifteenth Day of August, 1995

Attest:

BRUCE LEHMAN

Attesting Officer  Commissioner of Patents and Trademarks